United States Patent [19]

Emmons et al.

[11] Patent Number: 5,382,640

[45] Date of Patent: Jan. 17, 1995

[54] POLYMERS CONTAINING LATENT THIOL MONOMERS

[75] Inventors: William D. Emmons, Huntingdon Valley; Andrew W. Gross, Hatboro, both of Pa.

[73] Assignee: Rohm and Haas Company, Philadelphia, Pa.

[21] Appl. No.: 163,646

[22] Filed: Dec. 9, 1993

Related U.S. Application Data

[62] Division of Ser. No. 787,272, Nov. 4, 1991, Pat. No. 5,290,956.

[51] Int. Cl.$^6$ .................... C08F 28/04; C08F 120/38
[52] U.S. Cl. .................................. 526/266; 526/286; 526/289
[58] Field of Search ............... 526/286, 256, 270, 266, 526/289

[56] References Cited

U.S. PATENT DOCUMENTS 2,212,141  8/1940  Alderman .

OTHER PUBLICATIONS

Chem Abst, 86, 189153s (1977).

*Primary Examiner*—Christopher Henderson
*Attorney, Agent, or Firm*—David T. Banchik

[57] ABSTRACT

This invention relates to latent thiol monomers and their use in the synthesis of polymers. In addition, this invention relates to novel polymers and graft copolymers formed with these latent thiol monomers.

2 Claims, No Drawings

POLYMERS CONTAINING LATENT THIOL MONOMERS

This is a divisional of application Ser. No. 787,272, filed Nov. 4, 1991, now U.S. Pat. No. 5,290,956.

FIELD OF THE INVENTION

This invention relates to latent thiol monomers and their use in the synthesis of polymers. In addition, this invention relates to novel polymers and graft copolymers formed with these latent thiol monomers.

BACKGROUND OF THE INVENTION

"Latent thiol monomer," as used herein, is defined as a polymerizable monomer containing; at least one functional group polymerizable to form a homopolymer or copolymerizable with at least one first ethylenically unsaturated monomer to form a copolymer; and at least one protected thiol group, for example a thioester, preferably thioacetate. The term "latent" refers to the fact that the protected thiol group does not react in the homopolymerization reaction or the copolymerization reaction with the first ethylenically unsaturated monomer or monomers. After the homopolymerization or copolymerization is conducted, the protected thiol group can be deprotected, for example by a cleaving reaction, to form a thiol group pendant to the polymer chain. This thiol group so formed can then react in a second polymerization with at least one second ethylenically unsaturated monomer, to form a graft copolymer.

"Graft copolymers" as used herein, are defined as the macromolecule formed when polymer or copolymer chains are chemically attached to a polymeric backbone as side chains. Generally, in graft copolymers, the side chains are of different composition than the backbone chain. Due to the ability to chemically combine unlike polymeric segments in one molecule, graft copolymers have unique properties, making them particularly useful for their surface active properties, such as for example in stabilizing physical blends of otherwise incompatible polymeric or monomeric compounds.

The copolymer products of the present invention can be used directly in water-based emulsion coatings, elastomers, adhesives, caulks and mastics. Still further uses for these copolymers are as plastic additives for use as compatibilizers of polymer-polymer blends.

DESCRIPTION OF THE PRIOR ART

Canadian Patent 821,000 discloses a process for the preparation of block and graft copolymers. Unlike the aqueous process of the present invention, this is a nonaqueous process. The copolymers of Canadian Patent 821,000 are produced by first forming a backbone polymer containing epoxide functionality, reacting this backbone polymer with a mercaptan containing compound such as mercaptopropionic acid, then polymerizing another ethylenically unsaturated monomer in the presence of this backbone polymer such that the mercapto groups on the first polymer react with the vinyl groups of the polymerizing monomer, forming block and graft copolymers.

In addition, the process of Canadian Patent 821,000 is unlike the present invention in that in the present invention the latent thiol monomer reacts, in one step, with the at least one first ethylenically unsaturated monomer. The polymer chain formed during the first stage of the emulsion polymerization does not have to be reacted with an additional mercaptan containing compound, but can simply be deprotected to form a polymer chain containing a pendant thiol group.

U.S. Pat. No. 2,947,731 discloses a nonaqueous process of making vinyl benzene thioesters and their subsequent homopolymerization, or copolymerization with other vinyl monomers. In addition, it is disclosed that the thioester groups on these polymers and copolymers can be hydrolyzed to form the corresponding vinyl benzene thiol. However, nowhere is it taught or suggested to form graft copolymers, particularly by an emulsion polymerization process.

A key drawback to several of these techniques is the use of organic solvent as a required component of the polymerization, making it necessary to remove the solvent if a solvent-free product is desired. Other problems with all these techniques, whether polymerized in solvent or bulk polymerized using monomer as the solvent, are that they all yield a product with low molecular weight and all these prior art techniques lead to poor conversion of monomer to polymer.

In an article by Nakahama et al., *Makromol. Chem., Rapid Commun.* 10, 397–401(1989), and *Makromol Chem.* 192, 1891–1902(1991), an emulsion polymerization of styrene with isothiuronium salt containing monomer is reported. The salt is subsequently hydrolyzed to form polymers containing thiol groups. However, nowhere is the subsequent reaction of the thiol groups to form a graft copolymer taught or suggested. In addition, this cationic process results in severe compatibility problems with most anionic species.

SUMMARY OF THE INVENTION

Latent thiol monomers are polymerizable monomers containing; at least one functional group polymerizable to form a homopolymer or copolymerizable with at least one first ethylenically unsaturated monomer to form a copolymer; and at least one protected thiol group. After polymerization or copolymerization of the latent thiol monomers, the protected thiol group can be deprotected to produce a polymer having pendant thiol functional groups. In a subsequent or second stage polymerization, the pendant thiol function groups react with at least one second ethylenically unsaturated monomer to produce the graft copolymer.

DETAILED DESCRIPTION OF THE INVENTION

Latent thiol monomers are polymerizable monomers containing; at least one functional group polymerizable to form a homopolymer or copolymerizable with at least one first ethylenically unsaturated monomer to form a copolymer; and at least one protected thiol group. When the functional group is, for example, a vinyl group, the vinyl group either homopolymerizes or copolymerizes with at least one first ethylenically unsaturated monomer forming a copolymer. The protected thiol group on the latent thiol monomer does not react, or if it does react it only reacts to a limited extent, during the homopolymerization of the latent thiol monomer or the copolymerization with the at least one first ethylenically unsaturated monomer. After the polymerization or copolymerization, a polymer chain is formed with pendant protected thiol groups.

Examples of latent thiol monomers include compounds with the following structure;

$$R(C)_xOR_1SR_2$$

where R is a monovalent organic radical having polymerizable vinyl or olefinic groups; $R_1$ is a polyvalent organic radical; $R_2$ is an acyl radical (including acetoacetyl); and x is 0 or 1.

Additional examples of latent thiol monomers include vinyl benzyl thiolesters.

Specific examples of some latent thiol monomers include; allyl 3-mercaptopropionate thioacetate, (S-acetyl-3-mercaptopropyl)-2-methyl-2-propenoate, (S-benzoyl-3-mercapto-2-hydroxypropyl)-2-methyl-2-propenoate, (S-2,2-dimethylpropanoyl-3-mercapto-2-hydroxypropyl)-2-methyl-2propenoate, (S-acetyl-3-mercapto-2-acetoxypropyl)-2-methyl-2-propenoate, (S-acetyl-3-mercapto-2-hydroxypropyl)-2-methyl-2-propenoate, (S-acetyl-3-mercapto-2-acetoacetoxypropyl)-2-methyl-2-propenoate, (S-acetyl-3-mercapto-2-tetrahydropyranoxypropyl)-2-methyl-2propenoate, (S-acetyl-3-mercapto-2-(2-methoxy-2-propoxy)propyl)-2-methyl-2-propenoate, 2,3-epithiopropyl 2-methyl-2-propenoate, (S-acetyl-2-mercapto-3-acetoxypropyl)-2-methyl-2-propenoate, S-acetyl-(1-allyloxy-3-mercapto-2-hydropropane), S-benzoyl-(1-allyloxy-3-mercapto-2-hydroxypropane) and S-2,2-dimethylpropanoyl-(1 -allyloxy-3-mercapto-2-hydroxypropane). The more preferred latent thiol monomers are (S-acetyl-3-mercapto-2-acetoxypropyl)-2-methyl-2-propenoate, (S-acetyl-3-mercapto-2-hydroxypropyl)-2-methyl-2-propenoate, and the even more preferred is (S-acetyl-3-mercapto-2-hydroxypropyl)-2-methyl-2-propenoate.

When the latent thiol monomer is, for example, allyl 3-mercaptopropionate thioacetate, it may be prepared by first reacting 3-mercaptopropionic acid with allyl alcohol to form allyl 3-mercaptopropionate. This can then be reacted with acetic anhydride to form allyl 3-mercaptopropionate thioacetate.

When the latent thiol monomer is, for example, (S-acetyl-3-mercaptopropyl)-2-methyl-2-propenoate, it may be prepared by first reacting thiolacetic acid and allyl alcohol in the presence of t-butylhydroperoxide catalyst to form a thioacetate functional alcohol. This thioacetate functional alcohol product can then react with methacrylic anhydride to form the monomer.

When the latent thiol monomer is, for example, (S-acetyl-mercapto-2-hydroxypropyl)-2-methyl-2-propenoate, it may be prepared by reacting glycidyl methacrylate and thiolacetic acid. This reaction can be carried out in most solvents, but it is preferable to carry out the reaction in a 50% by weight ethanol/water solvent system. Purification of the monomer by removal of residual base catalyst leads to a more stable monomer. This can be accomplished by such techniques as, for example, vacuum treatment, flash chromatography on silica, and filtration through ion exchange resin. The more preferable technique is filtration through an ion exchange resin, preferably Amberlite ® IRC-50 ion exchange resin (a registered trademark of the Rohm and Haas Company).

The ethylenically unsaturated monomer useful in the copolymerization with the latent thiol monomer can be any ethylenically unsaturated monomer, for example; acrylate esters and acids; methacrylate esters and acids; acrylonitrile; methacrylonitrile; acrolein; methacrolein; vinyl aromatic compounds such as styrene, substituted styrene, vinyl pyridine and vinyl naphthalene; vinyl esters of organic acids, such as vinyl acetate; N-vinyl compounds such as N-vinyl pyrrolidone; unsaturated halogenated compounds such as vinyl chloride and vinylidene chloride; acrylamide, methacrylamide and substituted acrylamides and methacrylamides; polymerizable sulfonic acids and salts thereof such as styrene sulfonic acid. sodium vinyl sulfonate, sulfoethyl acrylate, sulfoethyl methacrylate and acryloamidopropanesulfonic acid (AMPS); vinyl ethers; or combinations thereof.

The latent thiol monomers of the present invention can be homopolymerized or copolymerized in all types of polymerization reactions well known to those skilled in the art, for example in a solution or emulsion polymerization. It is preferable, when forming graft copolymers of the present invention to use an aqueous, two stage emulsion polymerization process.

During the formation of the graft copolymer, the backbone portion of the copolymer is formed during a first stage of the aqueous emulsion polymerization. The backbone is formed by either the homopolymerization of at least one latent thiol monomer or the copolymerization of the at least one latent thiol monomer and the at least one first ethylenically unsaturated monomer.

The latent thiol monomer is contained in the first stage of the aqueous emulsion polymerization at a concentration of up to 100%, more preferably up to about 20%, even more preferably up to about 10%, and even more preferably up to about 3%, based on the total weight of the monomers in stage one.

The first stage emulsion polymerization should be run such that the protected thiol group from the latent thiol monomer remains substantially intact during the first stage polymerization. In addition, it is preferable to run the first stage emulsion polymerization reaction in an inert atmosphere, for example, in a nitrogen atmosphere.

Once the polymer chain with pendant protected thiol groups has been formed in the first stage of the aqueous emulsion polymerization, the polymer is subjected to a deprotection reaction, for example a cleaving reaction or thermal heating, whereby the protected thiol groups (latent thiol groups) are deprotected, converting them into free thiol groups.

When the protected thiol group of the polymer chains produced in the first stage emulsion polymerization are deprotected using a cleaving reaction, for example when the protected thiol group is thioacetate, any cleaving technique well known to those skilled in the art may be used. However, it is preferable to cleave the thioacetate group with, for example, ammonia, hydroxylamine, N-propylamine, diethylamine, morpholine, dimethylaminoethanol, and hydrazine. The more preferred cleaving agents are ammonia, dimethylaminoethanol and hydrazine and the even more preferred is hydrazine. Generally, the cleaving reaction is run at a temperature of from about 15° to 95° C. and more preferably from about 65° to 75° C.

Once the protected thiol groups have been deprotected to form pendant thiol groups, the polymer chain produced in the first stage emulsion polymerization can be isolated, for example by spray drying, used as is, or stored for further reaction at a later time. However, it is highly preferred that the second stage monomer emulsion be added directly to the polymer emulsion of stage one to form the graft copolymer. One of the key advantages of this process is that the polymer of stage one does not have to be isolated before reacting in stage two, and stage two can take place simply by adding stage two monomer.

In stage two of the aqueous emulsion polymerization at least one second ethylenically unsaturated monomer, preferably in the form of an aqueous emulsion, is added to a reaction mixture containing the polymer chain formed during the first stage of the aqueous emulsion polymerization. Because the polymer chain from the first stage is essentially a transfer agent containing pendant thiol groups, it is preferable to add all of the second stage monomer together at one time. However, if the second stage monomer is gradually added, some non-graft copolymer may form, yielding a mixture of graft copolymer and polymer derived from second stage monomer. This mixture may have some beneficial uses.

The at least one second ethylenically unsaturated monomer can be any of the ethylenically unsaturated monomers listed above for use as the at least one first ethylenically unsaturated first monomer.

The aqueous emulsion copolymerization technique of the present invention is based on a two stage polymerization where the mode of monomer addition in the first stage is not critical and a single addition of monomer in the second stage is preferred. The aqueous emulsion copolymerization techniques used in the present invention are well known to those skilled in the art. The temperature of the reaction in each of the two stages should be in the range of from about room temperature to about 150° C., more preferably from about 50° C. to 90° C.

An emulsifier can be used in the process of the present invention and can be of the general type of an anionic, cationic, or nonionic emulsifier. The more preferred emulsifiers are the anionic and the nonionic emulsifiers and the even more preferred are the anionic emulsifiers, such as sulfates and sulfonates, like sodium lauryl sulfate and sodium dodecyl benzene sulfonate. The amount of emulsifier used may be from about 0.05 to 10%, and more preferably from about 0.3 to 3%, based on the total weight of the monomers. Many other emulsifiers can be used and are well known in the emulsion polymerization art.

The latex particle size is controllable to be as small as from about 50 to 200 nanometers (nm) to as large as 800 nm or more by adjusting the type and level of emulsifier used. The particle size is preferably less than 500 nm.

It is advantageous to initiate and catalyze the reaction in each of the two stages in a conventional manner. Any commonly known free radical generating initiators can be used, such as persulfates, peroxides, hydroperoxides, peresters and azo compounds. Specific examples are benzoyl peroxide, tert-butyl hydroperoxide, azodiisobutyronitrile and sodium, potassium and ammonium persulfates. The more preferred are the sodium, potassium and ammonium persulfates which can be used by themselves, activated thermally, or in a redox system. When used in a redox system, reducing agents such as sodium formaldehyde sulfoxylate, isoascorbic acid and sodium bisulfite can be used along with a promoter, such as for example iron or others well known to those skilled in the art. Thermal initiation is more preferred. The amount of initiator will generally be in the range of from about 0.1 to 3.0% by weight, based on the total weight of the monomers.

The reaction conditions used in the second stage are dependant on the method of deprotection of the protected thiol group. For example, if a cleaving reaction utilizing ammonia is used to deprotect the protected thiol group, it is preferable to initiate the second stage polymerization thermally using ammonium persulfate or with redox initiators of tertbutylhydroperoxide and sodium formaldehyde sulfoxylate or isoascorbic acid. If hydroxylamine is used to deprotect the protected thiol group via a cleaving reaction, it is preferable to neutralize the amine with, for example, acetic acid, prior to the second stage polymerization. If hydrazine is used to cleave the protected thiol group, it is preferable to complex the hydrazine with 2,4-pentanedione prior to the stage two emulsion polymerization.

Additional initiator or catalyst systems may be added after stage two polymerization to reduce any residual monomer.

Generally, the aqueous emulsion formed containing the graft copolymer has a solids level of from about 20 to about 60%, based on the total weight of the aqueous composition. The graft copolymer products of this aqueous emulsion polymerization can be isolated, for example by spray drying, coagulation or other techniques well known to those skilled in the art. However, it is preferable to use the aqueous emulsion containing the copolymer as is.

The invention will now be illustrated by the following non-limiting examples.

Examples 1–4 Preparation of Latent Thiol Monomers

EXAMPLE 1

Preparation of 2-Propenyl-(S-Acetyl-3-Mercaptopropionate) (Allyl 3-Mercaptopropionate Thioacetate)

Step 1-Preparation of Allyl 3-Mercaptopropionate

TABLE 1

| Reagents for Example 1 - Step 1 | | |
|---|---|---|
| Allyl alcohol | 200 g. | 3.44 mole |
| 3-Mercaptopropionic acid | 250 g. | 2.36 mole |
| Methoxy Hydroquinone (MEHQ) | 1.0 g. | |
| Phenothiazine | 0.5 g. | |
| p-Toluenesulfonic acid | 1.0 g. | |
| Toluene | 250 g. | |

The reagents shown in Table 1 were mixed in a nitrogen flushed 1 liter flask fitted with a Dean Stark condenser, thermometer, and magnetic stirrer. The reaction mixture was heated to reflux until the theoretical amount of water had been collected. Under a nitrogen atmosphere, the Dean Stark condenser was removed and replaced with a Vigreaux column (24″) with distillation head. Allyl alcohol and toluene were removed from the reaction mixture at reduced pressure (20 mm Hg). The distillation was halted before the temperature reached 85° C., the distillation temperature at reduced pressure of allyl 3-mercaptopropionate.

Step 2-Conversion to allyl-3-mercaptopropionate thioacetate

The reaction mixture from step 1 was cooled under nitrogen and then diluted with 200 g. of methylene chloride. Then, 289 g. of acetic anhydride, along with a catalyst of 0.5 g. of 4-dimethylaminopyridine, were added to the reaction mixture. The reaction mixture was stirred for 1 hour at which time NMR analysis of a vacuum stripped aliquot indicated complete conversion to the desired thioacetate. The product was distilled at 132°–134° C. at 20 mm Hg to yield 355 g. of product (80%).

EXAMPLE 2

Preparation of (S-acetyl-3-mercaptopropyl)-2-methyl-2-propenoate

Step 1-Preparation of S-acetyl-3-mercaptopropanol

TABLE 2

| Reagents for Example 2 - Step 1 | | |
|---|---|---|
| Thiolacetic acid | 160 g. | 2.1 mole |
| Allyl alcohol | 150 g. | 2.58 mole |
| t-Butylhydroperoxide | 1.8 g. | |

To a 500 ml 3-neck flask equipped with thermometer, reflux condenser, addition funnel, and magnetic stirring was placed 130 g. of allyl alcohol. The addition funnel was charged with 130 g. thiolacetic acid and in a syringe was placed a solution of 1.8 g. t-butylhydroperoxide (t-BHP) in 20 g. allyl alcohol. Initially, 15 g. of thiolacetic acid was added to the kettle along with 2 ml. of the t-BHP solution. A slow cofeed of the remaining thiolacetic acid was begun along with the slow addition of the remaining t-BHP solution so as to maintain a reaction temperature of between 45°–55° C. Addition was complete in 1 hour, NMR analysis of an aliquot showed only the desired thioacetate alcohol along with residual allyl alcohol, Silver nitrate titration for residual thiolacetic acid showed essentially complete conversion, The excess allyl alcohol was stripped by a rotary evaporator and the product was used directly in the next step.

Step 2-Conversion to (S-acetyl-3-mercaptopropyl)-2-methyl-2-propenoate

TABLE 3

| Reagents for Example 2 - Step 2 | | |
|---|---|---|
| Thioacetate alcohol | 280 g. | 2.09 mole |
| Methacrylic anhydride | 400 g. | 2.59 mole |
| Tetrahydrofuran (THF) | 450 g. | |
| Phenothiazine | 2.0 g. | |
| 4-dimethylaminopyridine | 2.0 g. | |

The reagents listed in Table 3 were added to a 2 liter round bottom flask and the mixture was heated to reflux for 5 hours. The product was fractionally distilled at reduced pressure (1–3 mm Hg) through an Oldershaw column (30 in). In the initial distillation the fraction boiling between 80°–105° C. was collected. This fraction was then distilled a second time with the material boiling at 87°–94° C. (2 mm Hg) being collected. NMR analysis of this fraction showed minor impurities (5%) and the desired (S-acetyl-3-mercaptopropyl)-2-methyl-2-propenoate (249 g.; 60% yield).

EXAMPLE 3

Preparation of (S-acetyl-3-mercapto-2-hydroxypropyl) 2-methyl-2-propenoate

TABLE 4

| Reagents for Example 3 | |
|---|---|
| Glycidyl methacrylate (GMA) | 300 g. 2.11 mole |
| Thiolacetic acid | 159 g. 2.09 mole |
| Ethanol | 350 g. |
| Water | 300 g. |
| Butylated hydroxy toluene (BHT) | 2.0 g. |

TABLE 4-continued

| Reagents for Example 3 | |
|---|---|
| Ammonia (28%) | 0.5 g. |

To a 2 liter 4-neck flask fitted with a mechanical stirrer, thermocouple, and reflux condenser was added in the following order: 1) glycidyl methacrylate, 2) ethanol containing BHT, 3) water, 4) thiolacetic acid and 5) ammonia. Upon addition of the ammonia, the reaction began to exotherm slowly, the temperature rising at about 0.5° C./minute for the first 10 minutes, and increasing to 1° C./minute over the next 30-40 minutes. The reaction temperature peaked at 68°–72° C. and then began to cool.

NMR analysis of a vacuum stripped sample showed essentially complete conversion to (S-acetyl-3-mercapto-2-hydroxypropyl)-2-methyl-2-propenoate. Silver nitrate titration for unreacted thiolacetic acid indicated greater than 99% conversion of the thiol.

The product was pumped through a column of Amberlite IRC-50 weakly acidic resin (100 g. dry weight). The filtered product was stored at 5° C. where it exhibited less than 5% decomposition in 1 month.

EXAMPLE 4

Preparation of S-acetyl-(1-allyloxy-3-mercapto-2-hdroxypropane)

TABLE 5

| Allyl glycidyl ether | 40 g | 0.35 mole |
|---|---|---|
| thiolacetic acid | 30 g | 0.40 mole |
| triethylamine | 0.25 g | |
| tetrahydrofuran | 100 g | |

Allyl glycidyl ether and thiolacetic acid where dissolved in tetrahydrofuran and the triethylamine catalyst was added. The mixture was heated to reflux for 40 minutes at which time NMR analysis indicated complete conversion to S-acetyl-(1-allyloxy-3-mercapto-2-hydroxypropane).

EXAMPLE 5

Emulsion Polymerization

Stage One

Preparation of emulsion copolymer of 96.5 parts Butyl Acrylate/2 parts (S-acetyl-3-mercapto-2-hydroxypropyl)-2-methyl-2-propenoate/1.5 parts Methacrylic Acid To a 3 liter, 4 necked flask fitted with reflux condenser, thermometer and mechanical stirrer was added 570 g. of water and 7 g. of a 2.3% aqueous solution of sodium dodecylbenzenesulfonate. A monomer emulsion was prepared consisting of; 200 g. water; 10 g. of a 23% aqueous solution of sodium dodecylbenzenesulfonate; 675.5 g. of butyl acrylate; 14 g. of (S-acetyl-3-mercapto-2-hydroxypropyl)-2-methyl-2-propenoate (from Example 3); and 10.5 g. of methacrylic acid. A portion of this monomer emulsion (91 g.) was added to the kettle and the reaction mixture was then heated to 80° C. A solution of 1.0 g. ammonium persulfate in 34 g. of water was then added. After the initial exotherm subsided, the monomer emulsion was added to the kettle over 2.5 hours. The kettle was maintained at 80° C. for an additional 30 minutes and then cooled to 60° C. Then 0.4 g.

of t-butylhydroperoxide in 10 g. of water followed by 0.3 g. of sodium formaldehyde sulfoxylate in 10 g. of water was added. The theoretical yield was 45.5% solids and the actual yield was 45.4% solids.

Deprotection of Stage One Copolymer via a Cleaving Reaction

The stage one latex prepared above, 96.5 parts butyl acrylate/2 parts (S-acetyl-3-mercapto-2-hydroxypropyl)-2-methyl-2-propenoate/1.5 parts methacrylic acid (45.4% total solids) 400 g. solids, was placed in a 3 liter 4-necked flask (8 g., 0.037 mole of latent thiol groups present). The apparatus was then flushed with nitrogen. Hydrazine (2.0 g., 0.0625 mole, 1.69 equiv.) was added and the reaction mixture was heated to 70° C. After 1 hour, silver nitrate titration of a 0.25 g. solids aliquot showed quantitative liberation of thiol. Then, 2,4-pentanedione (6.88 g. 0.06875 mole) was added to complex with the hydrazine.

Stage Two

Emulsion Polymerization of 50 parts (96.5 parts BA/2 parts (S-acetyl-3-mercapto-2-hydroxypropyl)-2-propenoate/1.5 parts MAA)//50 parts Methyl Methacrylate Once deprotection was complete, the second stage monomer emulsion was prepared:

| MMA | 400 g. |
| Sipon WD | 0.7 g. |
| Water | 500 g. |

The emulsion was added to the latex and the temperature allowed to return to 60° C. Ferrous sulfate/EDTA solutions (1 ml of 0.15% solution) were added and the single shot polymerization was initiated by the addition of t-butylhydroperoxide (1.0 g. of a 70% solution in 10 g. water) followed by isoascorbic acid (1.37 g. in 10 g. water). An exotherm of 27° C. was observed over a 10 minute period. The reaction was allowed to cool to 60° C. and then 0.3 g. of t-BHP solution/5 g. water and 0.3 g. sodium formaldehyde sulfoxylate/5 g. water was added twice.

We claim:

1. A polymer comprising polymerized units of at least one latent thiol monomer selected from the group consisting of allyl 3-mercaptopropionate thioacetate, (S-benzoyl-3-mercapto-2-hydroxypropyl)-2-methyl-2-propenoate, (S-2,2-dimethylpropanoyl-3-mercapto-2-hydroxypropyl)-2-methyl-2-propenoate, (S-acetyl-3-mercapto-2-acetylpropyl)-2-methyl-2-propenoate, (S-acetyl-3-mercapto-2-hydroxypropyl)-2-methyl-2-propenoate, (S-acetyl-3-mercapto-2-acetoacetylpropyl)-2-methyl-2-propenoate, (S-acetyl-3-mercapto-2-tetrahydropyranyl)-2-methyl-2-propenoate, (S-acetyl-3-mercapto-2-(2-methoxy-2-propoxy))-2-methyl-2-propenoate, (S-acetyl-2-mercapto-3-acetylpropyl)-2-methyl-2-propenoate, S-acetyl-(1-allyloxy-3-mercapto-2-hydroxypropane), S-benzoyl-(1-allyloxy-3-mercapto-2-hydroxypropane) and S-2,2-dimethylpropanoyl-(1-allyloxy-3-mercapto-2-hydroxypropane), and, optionally, at least one ethylenically unsaturated monomer.

2. The polymer of claim 1 wherein the optional ethylenically unsaturated monomer is selected from the group consisting of acrylate esters and acids; methacrylate esters and acids; acrylonitrile; methacrylonitrile; acrolein; methacrolein; vinyl aromatic compounds; vinyl esters of organic acids; N-vinyl compounds; unsaturated halogenated compounds; acrylamide, methacrylamide and substituted acrylamides and methacrylamides; polymerizable sulfonic acids and salts thereof; and vinyl esters.

* * * * *